United States Patent [19]
Steinberg

[11] Patent Number: 5,564,435
[45] Date of Patent: Oct. 15, 1996

[54] NONINVASIVE COMPARTMENT MEASUREMENT DEVICE

[76] Inventor: Bruce Steinberg, 1325 San Marco, Ste. 200, Jacksonville, Fla. 32207

[21] Appl. No.: 575,968

[22] Filed: Jan. 5, 1996

Related U.S. Application Data

[60] Continuation of Ser. No. 273,014, Jul. 8, 1994, abandoned, which is a division of Ser. No. 54,456, Apr. 27, 1993, which is a continuation of Ser. No. 917,797, Jul. 20, 1992, abandoned, which is a continuation-in-part of Ser. No. 489,939, Mar. 6, 1990, abandoned, which is a continuation-in-part of Ser. No. 299,233, Jan. 23, 1989, abandoned.

[51] Int. Cl.$^6$ ............................. A61B 5/00; A61B 5/103; A61B 5/117
[52] U.S. Cl. ......................... 128/748; 128/774; 128/779; 128/782
[58] Field of Search .................... 128/645, 646, 128/650, 652, 721, 740, 748, 774, 779, 782, DIG. 25

[56] References Cited

U.S. PATENT DOCUMENTS

| | | |
|---|---|---|
| 1,619,491 | 3/1927 | Smith . |
| 3,680,386 | 8/1972 | Cannon . |
| 3,853,118 | 12/1974 | Schendel ............................. 128/2 S |
| 4,159,640 | 7/1979 | Lévêque . |
| 4,184,484 | 1/1980 | Wright et al. ........................ 128/748 |
| 4,209,023 | 6/1980 | Layton ................................. 128/748 |
| 4,421,124 | 12/1983 | Marshall ............................. 128/782 |
| 4,432,376 | 2/1984 | Huszor . |
| 4,502,491 | 3/1985 | Ender et al. . |
| 4,648,406 | 3/1987 | Miller ................................. 128/674 |
| 4,709,690 | 12/1987 | Haber ................................. 128/1 R |
| 4,711,248 | 12/1987 | Steuer et al. ........................ 128/748 |
| 4,727,887 | 3/1988 | Haber ................................. 128/748 |
| 4,741,345 | 5/1988 | Matthews et al. ................... 128/675 |
| 4,858,620 | 8/1989 | Sugarman et al. .................. 128/774 |
| 4,869,265 | 9/1989 | McEwen ............................. 128/774 |
| 5,038,795 | 8/1991 | Roush et al. . |

OTHER PUBLICATIONS

Ostrander, L. E.; Lee, B. Y.; and Cui W.: Noninvasive Method for the Assessment of Anterior Compartment Syndrome; American College of Surgeons, Oct. 23, 1988.
Ostrander, L. E.; Cui, W.; Croskopf, R.; Lee, B. Y.: Viscoelasticity of Bulk Limb Tissue; IEEE Engineering and Medicine and Biology Society, 11th Annual International Conference, Jun. 1989.
David Freedman, et al.; *Statistics;* 1978; pp. 146–167.
Thomas E. Whitesides, Jr., M.D., et al.; "Tissue Pressure Measurements as a Determinant for the Need of Fasciotomy"; 1975; pp. 43–51 [*Clin. Orthop.,* 113:43].

*Primary Examiner*—John G. Weiss
*Assistant Examiner*—K. M. Reichie
*Attorney, Agent, or Firm*—Irell & Manella LLP

[57] ABSTRACT

An apparatus and method are disclosed for noninvasively diagnosing limb compartment syndrome by measuring a quantitative modulus of hardness. In the preferred embodiment, a low friction piston probe mounted within a platform is applied against a limb compartment. Pressure within the piston probe is increased while measuring the displacement of the piston plunger for each pressure applied. The relationship of incremental pressures in the piston to the displacements of the piston plunger are plotted and a linear regression analysis is performed whose slope forms a quantitative modulus of hardness. In an alternate, completely automated, continuous embodiment, a circumferential cuff secures the piston probe mounted within the a platform against the limb compartment, while the quantitative hardness modulus is formulated.

4 Claims, 5 Drawing Sheets

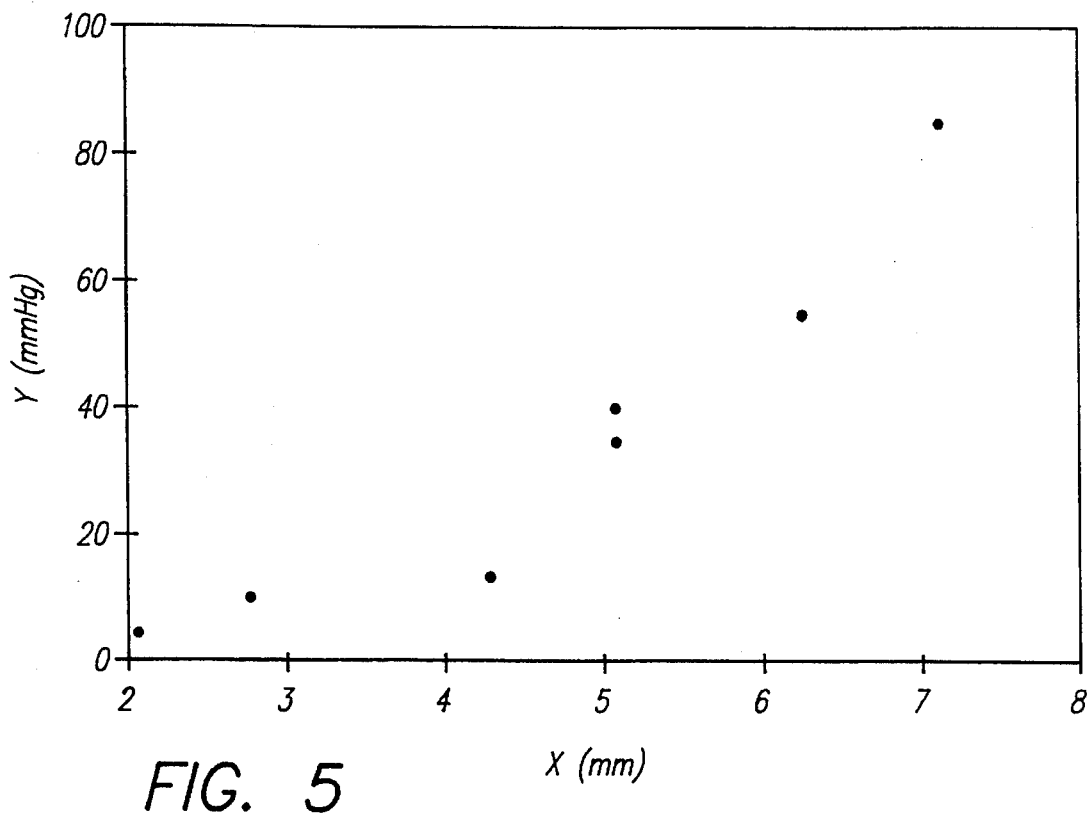
FIG. 5
FIG. 6
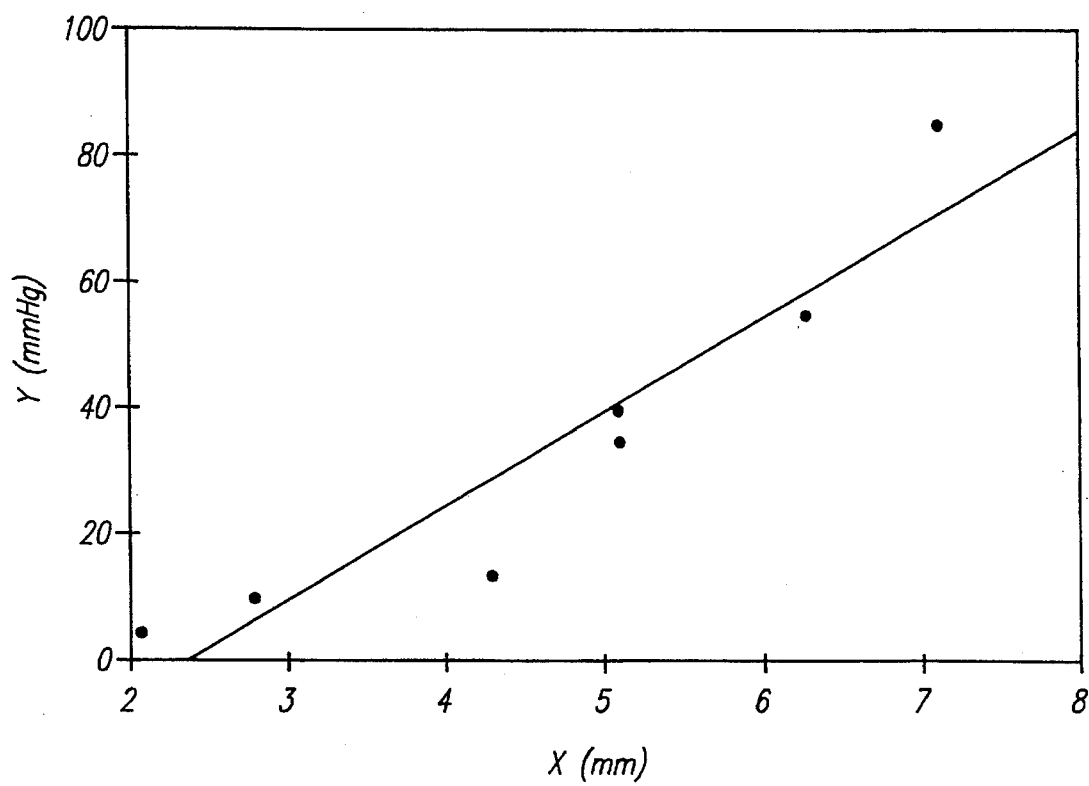

NONINVASIVE COMPARTMENT MEASUREMENT DEVICE

REFERENCE TO RELATED APPLICATIONS

This application is a continuation of application Ser. No. 08/273,014, filed Jul. 8, 1994, now abandoned, which is a division of application Ser. No. 08/054,456, filed Apr. 27, 1993, which is a continuation of application Ser. No. 07/917, 797, filed Jul. 20, 1992, and now abandoned, which is a CIP of application Ser. 07/489,939, filed Mar. 6, 1990, and now abandoned, which is a CIP of application Ser. No. 07/299, 233, filed Jan. 23, 1989, and now abandoned.

FIELD OF THE INVENTION

The invention pertains to the measurement of hardness of the tissue of a limb by using a noninvasive technique. This technique will be a warning device to safeguard against the development of compartment syndrome by relating hardness to intracompartmental interstitial pressure.

BACKGROUND OF THE INVENTION

Presently, the diagnosis of compartment syndrome is made by the direct measurement of intracompartmental interstitial pressure based on a technique developed by Dr. Thomas E. Whitesides, Jr. In this technique, a small amount of fluid is injected into a compartment (i.e. the volar compartment of the forearm). The pressure necessary to advance the fluid into the compartment is the measurement of the pressure of the compartment. If the intracompartmental interstitial pressure should increase to within 30 mmHg of the diastolic pressure, this could result in irreversible damage to the tissue within the compartment. The treatment for such a condition is emergency surgical release of the facia, overlying the muscle, which is constricting the compartment. Delay in the diagnosis of compartment syndrome and subsequent delay in performing the fasciotomy can result in needless loss of function, contracture, and possible amputation.

The decision to perform a fasciotomy for a suspected compartment syndrome is frequently difficult. In the classic article by Dr. Thomas E. Whitesides, Jr., "Tissue Pressure Measurements as a Determinant of the Need for Fasciotomy", Clin. Orthop., 113:43, 1975, even if physicians are well versed in the signs and symptoms of compartment syndrome, the clinical analysis sometimes is indefinite and confusing, resulting in delay in performing the fasciotomy.

According to Dr. Whitesides Jr., the one factor that must be present in a compartment syndrome is increased intracompartmental interstitial pressure. Therefore, the effectiveness of the fasciotomy is based on relieving this pressure and reestablishing tissue perfusion. In order to effectively diagnose compartment syndrome, a technique for measuring tissue pressure has been established. For details of the technique of direct intracompartmental interstitial pressure measurement, refer to the article cited above by Dr. Thomas E. Whitesides, Jr. Presently, there are two electronic devices available that are based on principles outlined by Dr. Whitesides, Jr. (Ace, Los Angeles, Calif.; Stryker, Kalamazoo, Mich.).

There are several disadvantages related to the Whitesides technique. First, the technique is difficult to apply continuously, second, it cannot be used to measure compartment pressure within a cast and third, it is invasive.

These disadvantages are now examined separately. First, many compartment syndromes are an evolving phenomenon. One measurement may not safely establish an ensuing compartment syndrome. A continuous noninvasive monitor of intracompartmental interstitial pressure would be very useful for assessing the possibility of an evolving compartment syndrome.

Second, for infants or those patients who have difficulty communicating, an assessment of intracompartmental interstitial pressure within a cast would be very beneficial. If pressure within the cast increases above 30 mmHg within the diastolic pressure, the cast should be removed. Obviously, the Whitesides technique which incorporates the use of a needle could not be used for detecting compartment syndrome for extremities which are within casts, unless the cast is removed. The removal of a cast, however, is time consuming and may lead to loss of fracture alignment.

Third, the invasive nature of the Whitesides technique places risk of injury to vital structures with each measurement. Puncture of the skin is painful and may also lead to infection. Finally, the invasive technique cannot be applied by non M.D. personnel such as nurses and medical assistants. With these disadvantages in mind, a noninvasive device and technique have been developed.

Compartment syndrome occurs in skeletal muscles enclosed by osseofascial boundaries. The condition develops when accumulating fluid creates high interstitial pressure within the closed osseofascial space, reducing perfusion of surrounding tissues below a level necessary for viability. As the interstitial pressure within the compartment increases, the expansion of the compartment is limited by the compliance of the osseofascial envelope. Like a balloon about to burst, the envelope becomes less and less compliant as the interstitial pressure increases. The change in compliance can be detected by palpation. The inventor, Dr. Bruce Steinberg, has quantitatively measured palpation (linear regression of force applied/to volume displaced) and has shown that a close correlation exists between this quantitative modulus of hardness and the interstitial pressure within a compartment. By measuring a quantitative hardness modulus one can noninvasively monitor interstitial intracompartmental pressures and diagnose compartment syndrome.

Another prior art device is described in Leveque et al., U.S. Pat. No. 4,159,640, which discloses a method and apparatus for measuring hardness of a material. This device comprises, "a support to rest on the material to be tested; a feeler carried by said support and arranged to bear on the said material with a predetermined force; and means for selectively and automatically detecting the displacement of the feeler only for a predetermined value P of the bearing pressure of the apparatus on the material." This measurement of hardness is inaccurate. Hardness measurements are more accurate when a modulus is formulated. The quantitative hardness modulus is the slope of the linear regression of multiple incremental measurements of force applied (y axis) to the displacements (x axis) caused by each incremental force. The device disclosed by Leveque et al, has no means of formulating a quantitative hardness modulus, only one force and displacement are measured. In order to eliminate the devastating outcome of a false negative diagnosis of compartment syndrome, or the unnecessary surgical procedure of a false positive diagnosis of compartment syndrome, the accuracy of the hardness measurement is paramount. This quantitative measurement is made accurate by formulating a hardness modulus based on multiple data points. The present invention overcomes the inaccuracy of the Leveque et al. device by obtaining a hardness modulus based on multiple data points.

Another prior art device is described in Roush et al., U.S. Pat. No. 5,038,795, which discloses a method and apparatus for the measurement of muscle tone. The device comprises a means of applying a force through a pair of calipers which pinch a muscle group (usually the superficial posterior compartment of the leg), and a means of measuring the resultant displacement of the muscle group. This device was designed for the diagnosis of medical diseases related to muscle tone, not the diagnosis of compartment syndrome. A caliper device that measures hardness is unable to be applied in the majority of compartments at risk for compartment syndrome. In the leg, for example, three of the four compartments (the anterior, lateral, and deep posterior compartments) can not be measured for hardness using the Roush device because the calipers would include the tibia bone making the measurement inaccurate. In addition, in the upper extremity, the thenar, hypothenar, carpal tunnel, and distal forearm all can not be pinched without including a bony structure. These compartments are assessed clinically for compartment syndrome by palpation not pinch. By using a device that unilaterally pushes on a muscle compartment while recording force applied to displacement measured, one can quantitatively assess hardness for all the compartments of the upper and lower extremities. The present invention overcomes the weakness of the Roush et al. device by unilaterally applying a pressure to a compartment and measuring the compression of the compartment, in effect quantitatively palpating the compartment.

SUMMARY OF THE INVENTION

The present invention is a noninvasive technique which monitors the condition of tissue. More particularly, a noninvasive technique for diagnosing and monitoring compartment syndrome. In the preferred embodiment of the invention, a low friction piston probe mounted within a platform, attached to a holding brace and pressure syringe are used to monitor the hardness of a limb compartment.

More particularly, the preferred embodiment of the invention includes an apparatus and method for evaluating the condition of tissue within a limb. The method comprises the following steps. First, applying the apparatus to a limb with a known force of application, second, incrementally changing the pressure in the piston and measuring the displacement of the piston plunger for each force applied. The method also includes the step of determining the relationship of the multiple data points of pressure applied to compression measured, formulating a quantitative hardness curve. Additionally, the present invention performs a linear regression analysis on the multiple data points whose slope is the quantitative hardness modulus.

BRIEF DESCRIPTION OF THE DRAWINGS

FIG. 5 is the plot of the multiple data points of piston (F) pressures Y to the plunger (K) displacements X.

FIG. 6 is the plot of the line formed by the linear regression analysis of (X,Y) data points.

DETAILED DESCRIPTION OF THE PREFERRED EMBODIMENT

Figure 1:
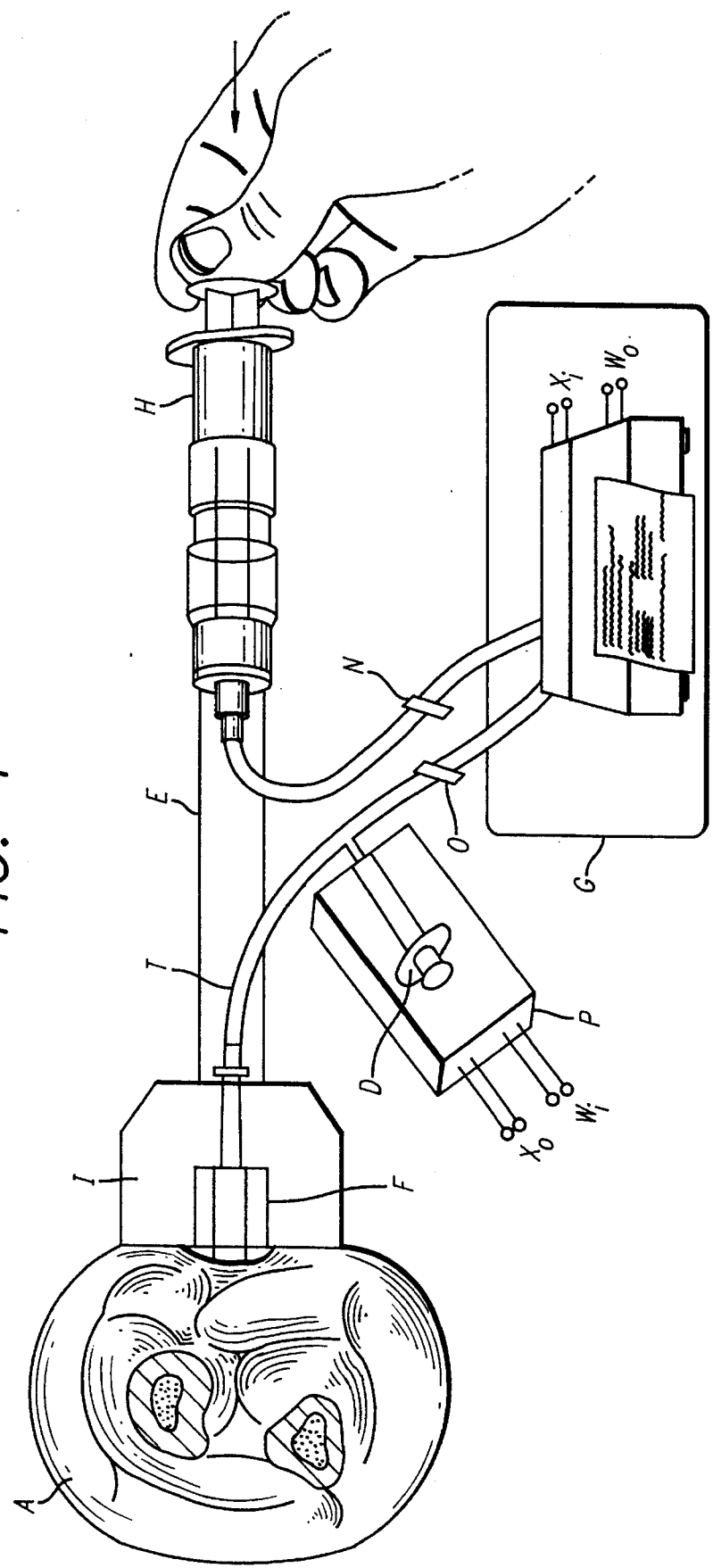
FIG. 1 is a diagram of the preferred embodiment of the invention.
Figure 2:
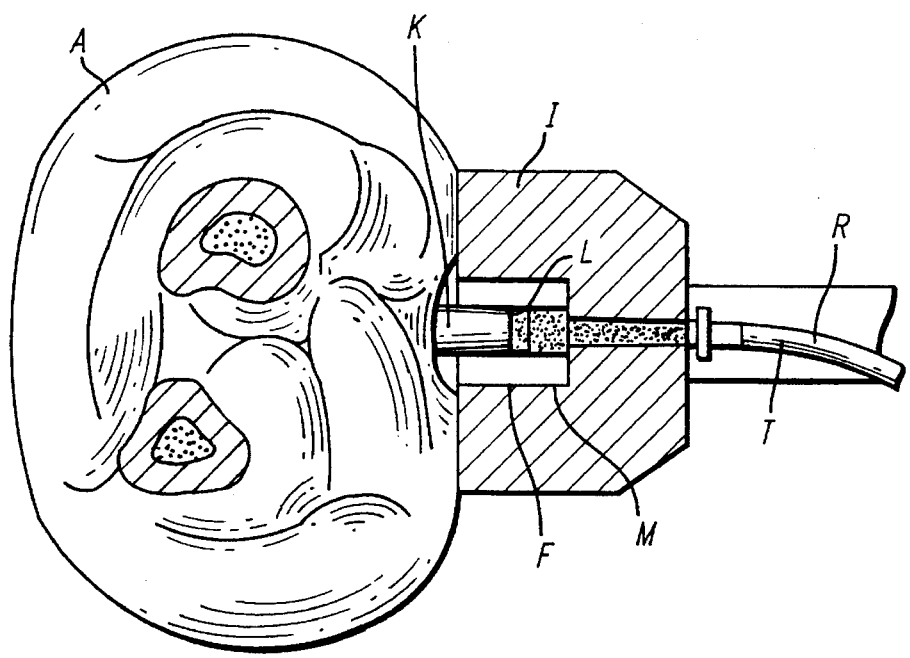
FIG. 2 is a more detailed depiction of the piston (F) and platform (I) of the preferred embodiment.

Referring to FIGS. 1&2, an embodiment of the invention is shown. A low friction piston probe (F), constructed with a sapphire plunger $(K)_{(only\ FIG.\ 2)}$, a teflon seal $(L)_{(only\ FIG.\ 2)}$, and a hard plastic housing $(M)_{(only\ FIG.\ 2)}$, is mounted within a platform (I). This apparatus is secured to a brace (E). Attached to the brace (E) is a pressure syringe (H) for applying the above apparatus against a limb compartment (A). The force applied to the syringe (H) secures the platform (I) against the limb (A). This force is converted to an electrical signal Z by a pressure transducer (N) (Sen Sym, BPO1, Sunnyvale, Calif.), and recorded by a computer (G). When the force of application of the apparatus (pressure in the syringe H) reaches a predetermined level $Z_o$, measurement of limb compartment hardness is obtained, by obtaining the slope of the line formed by measuring piston (F) pressure and displacement of the plunger within piston (F).

Limb compartment hardness is obtained by incrementally increasing pressure within the piston probe (F) and measuring the displacement of the plunger (K). By using an incompressible fluid $(R)_{(only\ FIG.\ 2)}$ (non-sterile water) and rigid tubing (T) (Norton, Tygon Tubing, Akron Ohio), the amount of fluid advanced by syringe (D) is directly proportional to the advancement of the plunger (K). The pressure $P_o$ within the tubing (T) is converted to an electrical signal Y by pressure transducer (0) (Sen Sym, BPO1, Sunnyvale, Calif.) and recorded by the computer (G).

Figure 3:
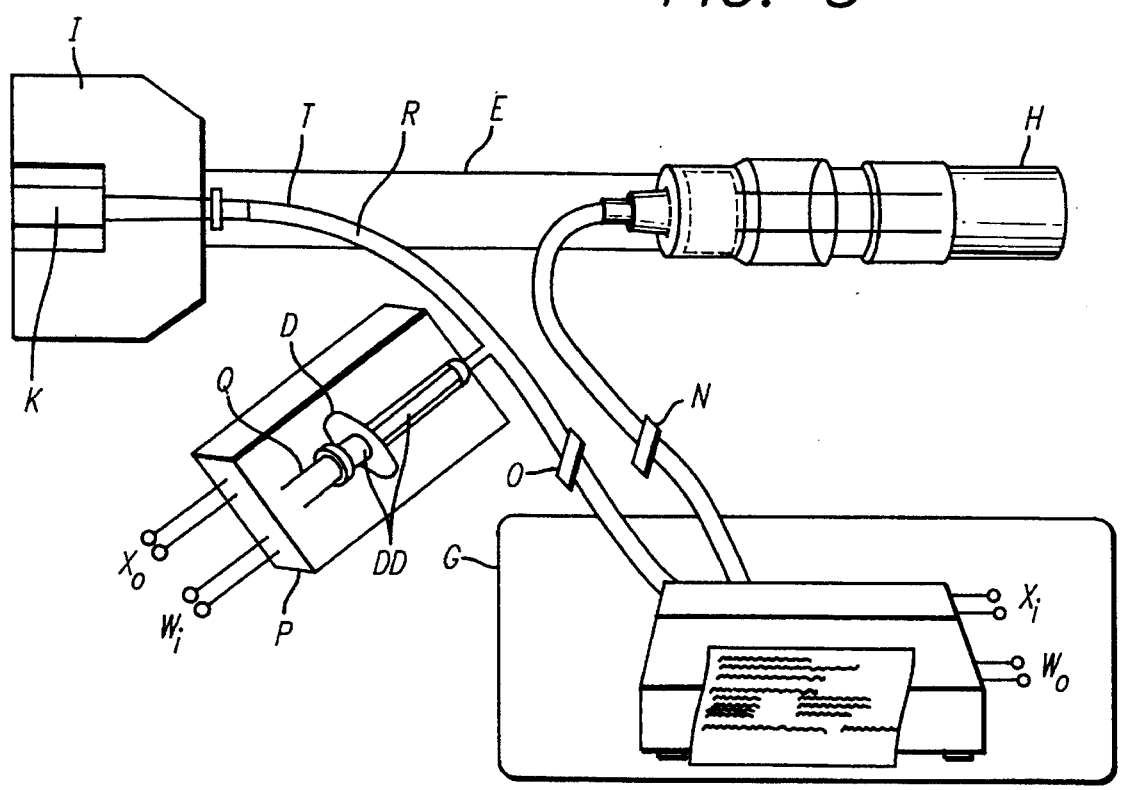
FIG. 3 is a more detailed depiction of the automated syringe compression device (P) of the preferred embodiment.

Referring to FIGS. 1&3, an automated device (P) (Baxter, Intravenous Drug infuser, Boston, Mass.) will create pressure $P_o$ in tubing (T) by compressing syringe plunger (DD) with a ram (Q) forcing an incompressible fluid (R) to move the plunger (K). This will occur when the pressure in the syringe (H) reaches a predetermined value $Z_o$ causing the computer (G) to signal $W_o$ the automated pressure device (P) $W_i$ to incrementally compress syringe (D). The movement of the plunger (K) against the extremity (A) compresses the tissue of the compartment having the suspected compartment syndrome. As the pressure $P_o$ increases, a series readings $L_i$ can be taken of the location of the plunger (K) where $L_i - L_o = L$. By using an incompressible solution and rigid tubing, the amount of fluid advance in the syringe (D) will be directly proportional to the advancement of the plunger (K) of the probe (F). One can therefore use the amount of fluid advancement in the syringe (D) to calculate the L in the plunger (K). The measurement of the fluid advancement in syringe (D) is determined by the value of the original position of the syringe plunger (DD), less the final position of the syringe plunger (DD). The amount of movement of the syringe plunger (DD) is proportional to the voltage output $X_o$. Output voltage $X_o$ is input into computer (G) $X_i$. In addition, the corresponding pressure $P_o$ within the tubing (T) and probe (F) is converted to an electrical signal Y by pressure transducer (O) and recorded by the computer (G). By using an incompressible fluid and rigid tubing and requiring that the system be closed, the pressure in the probe (F) is equal to the pressure within the tubing (T).

From these various readings the quantitative hardness modulus is formulated, it can be derived as follows:

Quantitative Hardness Modulus = $QH$ $QH$ = Stress/Strain where;

Strain = change of volume of the limb displaced by plunger($K$)/Original volume

= $\Delta V/V_o = \Delta L/L_o \times \frac{\text{cross section plunger }(K)}{\text{cross section plunger }(K)} = 1$ = $\Delta V/V_o = \Delta L/L_o \times 1$; $\Delta L$ = change in plunger ($K$) position $L_o$ = original position of plunger ($K$)

= $\Delta L/L_o$

Stress = change in pressure applied to the Limb ($A$) = $\Delta P$ $QH$ = Stress/Strain = $\Delta P/\Delta L/L_o$ When the fluid used in the system is incompressible and the tubing is rigid;

$\Delta L/L_o \approx$ change in Volume of the fluid in syringe (D); where

K=proportionality constant

VD=change in Volume of the fluid in syringe (D)

$\Delta L/L_o = K \times VD$;

$QH = \Delta P/(K \times VD)$;

$QH = \Delta P/VD$;

where $\Delta P = Y$ electrical value, and ($K \times VD$)=$X$ electrical value ($X$ electrical value is equal to $X_o$, which is equal to $X_1$);

$QH = Y/X$

The computer (G) will plot the multiple data points formed by the (X,Y) values. (FIG. 5) Experimental studies by Dr. Steinberg have shown that the relationship between the pressure applied to the displacement is linear, therefore the plot that best fits the points is a line. (FIG. 6) Linear regression analysis (refer to Freedman, Pisani, and Purves; *Statistics*; W. W. Norton, New York, 1978, pp.146–167) formulates the equation of the line that best fits the data points. The slope of the line is the quantitative hardness QH. Several computer programs exist for performing linear regression analysis, those skilled in numerical analysis are readily familiar with these computer packages. The computer will have the capability of displaying, storing, and comparing the value of QH.

Figure 4:
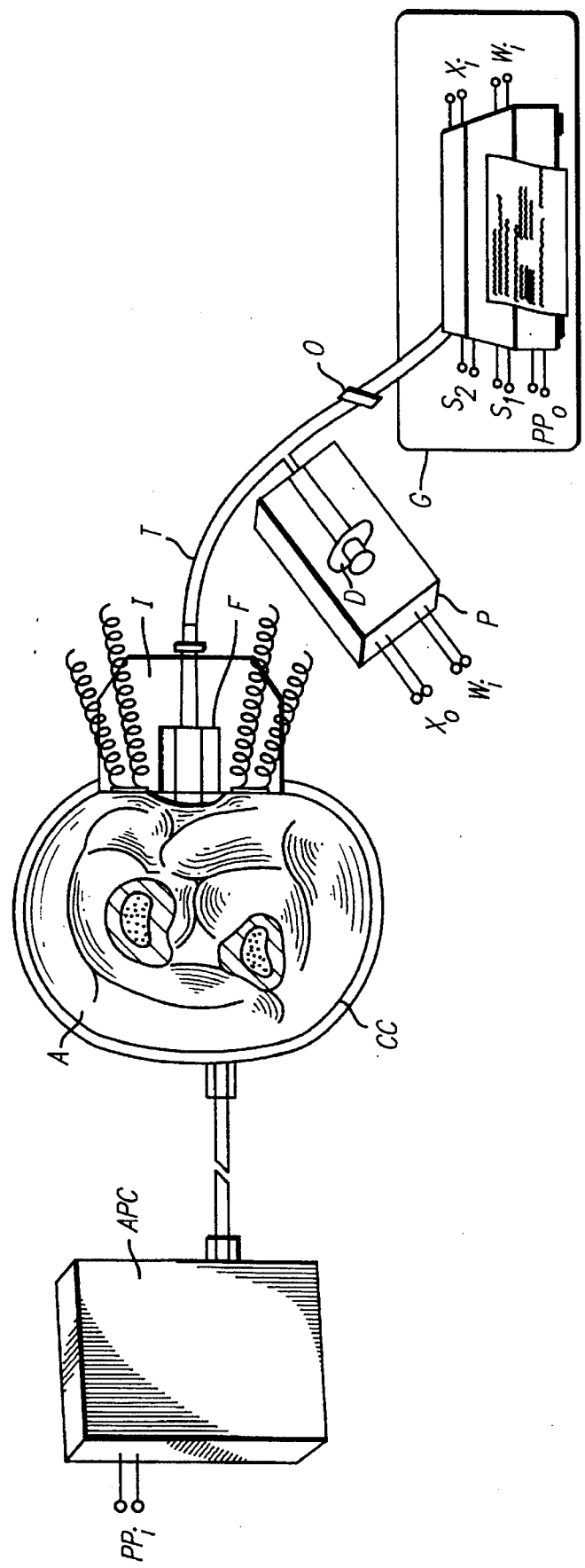
FIG. 4 is a diagram of an alternate, completely automated, continuous embodiment of the invention.

Referring to FIG. 4, an alternate embodiment of the invention is shown. In the embodiment brace (E) and pressure syringe (H) which secure the platform (I) against the limb are eliminated. The platform (I) is now secured by a circumferential cuff (CC). Like a blood pressure cuff, this circumferential cuff (CC) can be inflated to a predetermined pressure by an automated pressure pump (APC) (Data Scope, Paramus, N.J.) securing the platform (I) against the limb.

Figure 7:
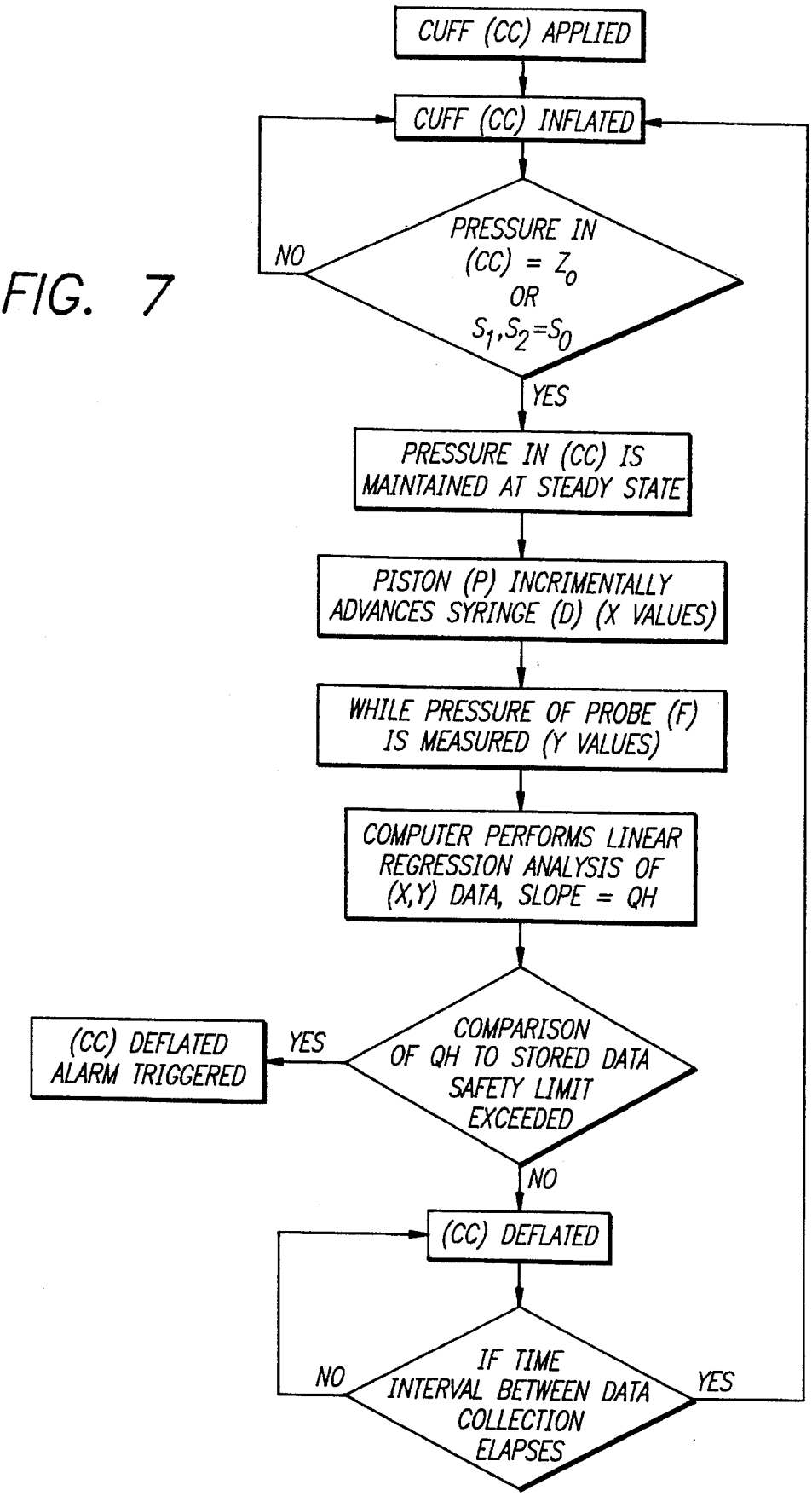
FIG. 7 is a flow chart depicting the decision process of the alternate, completely automated, continuous embodiment.

With this embodiment, the system is completely automated and can be used continuously (refer to FIG. 7). A patient suspected of having a compartment syndrome or one that may develop the syndrome will have the cuff (CC) applied. The computer (G) signals $PP_o$ the automated pressure cuff (APC) $PP_i$ to inflate the pressure cuff (CC). When this pressure reaches a pre-determined value, a quantitative hardness modulus is formulated by obtaining the slope of the line formed by measuring piston (F) pressure and the displacement of the plunger within piston (F). When the pressure in the cuff reaches a predetermined value $Z_o$ or when pressure sensors $S_1$ and $S_2$ (Sen Sym, Scc100, Sunnyvale, Calif.) measure predetermined pressures $S_o$, the computer (G), while maintaining a steady state pressure $Z_o$ in the cuff (CC), will signal $W_o$ device (P) $W_i$ to obtain quantitative hardness measurements. As in the previous embodiment, the quantitative hardness modulus QH is derived through the slope of the linear regression analysis of the piston (F) pressures Y to the plunger (K) displacements X. Values of QH are displayed, stored and compared to previous values. When the quantitative hardness modulus reaches a predetermined value or if there is a significant change in value, then an alarm will be triggered, informing the patient or physician of a possible compartment syndrome. After each quantitative hardness measurement, the cuff (CC) is deflated.

The computer (G) can be programmed to control the sampling rate of the apparatus depending on the clinical situation determined by the medical personnel. If a quickly progressing compartment syndrome is anticipated, then a frequent sampling (i.e. every 10 minutes) can be obtained. If the compartment syndrome is not anticipated to occur rapidly, then a slower sampling rate (i.e. once every 6 hours) may be indicated.

The present invention has been shown in the two embodiments described but should not be limited thereto. Alternate embodiments of various components of the system may be employed.

What is claimed is:

1. A method for evaluating hardness of tissue of a limb for the purpose of diagnosing compartment syndrome, said method comprising the steps of:

applying a piston to a limb compartment with a predetermined force, incrementally applying pressure to the tissue of the limb with a plunger within said piston in order to compress the limb, measuring the pressure in the piston while also measuring displacement of the piston plunger, and plotting the relationship of the incremental pressure applied to the displacement measured.

2. The method in claim 1 wherein said step of plotting the relationship of the pressure applied to the displacement measured further including the step of performing linear regression analysis.

3. A method for evaluating hardness of tissue of a limb for the purpose of diagnosing compartment syndrome, comprising the steps of:

applying a piston to a limb compartment with a force, applying pressure to the tissue of the limb with a plunger within said piston in order to compress the limb, measuring the pressure in the piston and measuring the displacement of the piston plunger, and plotting the relationship of the pressure applied to the displacement measured.

4. The method of claim 3, wherein said step of plotting the relationship of the pressure applied to the displacement measured further includes the step of linear regression analysis.

* * * * *